United States Patent [19]
Anderson et al.

[11] 4,067,994
[45] Jan. 10, 1978

[54] IRON METHIONINE COMPLEX SALTS

[75] Inventors: Dean R. Anderson, Excelsior; Mahmoud M. Abdel-Monem, St. Paul, both of Minn.

[73] Assignee: Zinpro Corporation, Chaska, Minn.

[21] Appl. No.: 670,746

[22] Filed: Mar. 26, 1976

[51] Int. Cl.$^2$ ............................................. A61K 31/295
[52] U.S. Cl. ................................. 424/295; 260/439 R
[58] Field of Search ...................... 260/439 R; 424/295

[56] References Cited

U.S. PATENT DOCUMENTS

| 2,955,981 | 10/1960 | Linkenheimer | 424/295 |
| 2,957,806 | 10/1960 | Rummel | 424/295 |
| 3,002,985 | 10/1961 | Imado | 260/439 R |
| 3,076,747 | 2/1963 | Hallberg | 424/295 X |
| 3,259,500 | 7/1966 | Barnhart et al. | 424/295 X |

FOREIGN PATENT DOCUMENTS 1,801,331   5/1970   Germany ............................ 424/295

OTHER PUBLICATIONS

Albert, Biochem. J. 47, 531–537 (1950).
Perrin, J. Chem. Soc. pp. 3125–3128 (1958).
Perrin, J. Chem. Soc. pp. 290–296 (1959).
Chemical Abstracts, 49 14554c (1955).

Primary Examiner—Helen M. S. Sneed
Attorney, Agent, or Firm—Zarley, McKee, Thomte, Voorhees & Sease

[57] ABSTRACT

Novel complex salts wherein the cation of the salt is a complex between iron and methionine. These salts are useful for nutritional supplementation to provide iron and methionine, both in a form which effectively increases the bioavailability of these compounds to animals.

11 Claims, No Drawings

IRON METHIONINE COMPLEX SALTS

BACKGROUND OF THE INVENTION

The importance of an adequate dietary supply of iron to both animals and humans has been unequivocally documented in the literature. Indeed the literature, both patent and otherwise, is replete with reports of the occurance of iron-deficiency anemia and its reversal by intake of iron. Iron is essential to the elementary metabolic process in the cell. It is responsible for the transport of molecular oxygen in higher organisms. Animals or humans deficient in iron will become anemic and will have a decreased capability for transporting oxygen.

In addition, it is essential that the body be provided with adequate levels of essential amino acids. Amino acids are the building blocks of body protein with the protein itself comprised of a plurality of amino acid molecules each bound to the other in a repetitive fashion. It is essential for normal growth rate of man and other animals that an adequate level of the amino acids be present in the diet. Moreover, certain of these amino acids cannot be formed by the body and must be ingested. Methionine is an example of one of the essential amino acids necessary for body protein building.

While the importance of adequate dietary levels of iron has long been documented and known, most iron compounds do not provide this element in a form which effectively allows it to be absorbed, distributed and utilized efficiently by animals. For example, the mere feeding of a conventional iron salt such as ferrous sulfate may not significantly increase the level of iron or significantly decrease an iron-deficiency condition because iron has to be transported through membranes which do not readily permit iron ions to pass. It is believed that iron is absorbed and transported in the form of complexes of the metal ion with organic molecules. Therefore, conventional inorganic iron salts such as ferrous sulfate must be converted to organic complexes to be utilized nutritionally by animals.

This invention has as its object the preparation of novel iron methionine complex salts wherein the iron is in a form which can be readily absorbed after ingestion, distributed and utilized efficiently by animals.

Yet another object of this invention is to provide novel compounds which contain methionine as part of a cation complex with the methionine present in a form which can be readily absorbed after ingestion.

Yet another object of this invention is to provide as a feed supplement new iron methionine complex salts wherein the cation of the salt is comprised of an iron methionine complex with the result being that the new feed supplement can be fed with greater efficiency from the standpoint that more of the iron and the methionine will be absorbed, distributed and utilized by the animal than would occur if conventional salts of iron and the compound methionine per se were fed as feed supplements.

The method of accomplishing these and other objects will become apparent from the following description of the invention.

SUMMARY OF THE INVENTION

Ferric and ferrous methionine complex salts wherein the cation of the salt is comprised of an iron methionine complex were prepared. The iron may be ferric or ferrous iron and the complexes may be 1:1 or 1:2 iron methionine complexes. The anion of the complex salt is preferably inorganic and can be, for example, a halide, phosphate, sulfate or the like. These iron-methionine complexes are useful feed supplements as a nutritionally available source of iron and methionine.

DETAILED DESCRIPTION OF THE INVENTION

An important aspect of the compounds of this invention is that these compounds are soluble in water and in the pHs existing in the intestinal tracts of animals. Thus methionine, for example, is relatively difficult to dissolve in water. The compounds of this invention which include methionine as a portion of the cation, in the form of complex, are all very water soluble.

The water soluble methionine ferric ion complex salts have the formula:

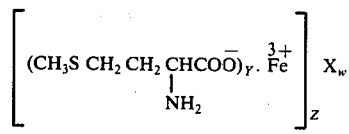

wherein Y is a whole integer and is 1 or 2, X is an inorganic anion, and Z and W are whole integers selected to electrostatically balance the cationic and anionic charges of the complex salt.

As seen in the above presented formula, Y may be either 1 or 2, depending upon whether the iron methionine complex is a 1:1 complex or a 1:2 complex. While both 1:1 and 1:2 iron methionine complex salts may be utilized in this invention, the preferred form is the 1:1 complex since the increased levels of methionine provided by the 1:2 complexes does not increase the bioavailability of iron.

The selection of an anion is not critical and X, representing the anion in the previously presented equation, can be an inorganic anion or an organic anion, a monovalent anion, a divalent anion or a polyvalent anion. Preferably the source of the anion X is an inorganic acid or acetate. Suitable inorganic anions can be found in the halogen acid family, the sulfates, and the phosphates. Preferably where the anion is an inorganic anion, it is selected from the group consisting of monovalent anions such as halides, hydrogen sulfate and dihydrogen phosphate.

The anion can also be an organic anion moiety derived from an organic acid. It can be derived from simple aliphatic carboxylic acids, both monobasic carboxylic acids and dibasic carboxylic acids.

In the previously presented emperical formula, Z represents the number of cations needed to provide an overall neutral charge on the complex salt with W being the same representation for the anion.

It is important to note that the compounds of this invention are complex salts with the cation comprising the complex of iron and methionine. This is to be distinguished from a conventional salt such as ferrous sulfate wherein the cation is comprised only of iron.

In the compounds described in this invention iron, which has a coordination number of 6, will form an octahedral coordination complex in which methionine is a bidentate ligand. In the 1:1 iron methionine complexes the methionine will occupy two of the coordination valencies of iron and the other four coordination valencies will be occupied by the acid sulfate anions and water. In the 1:2 iron methionine complexes the methionine molecules will occupy 4 of the coordination valencies of iron and the other two valencies will be occupied by the acid sulfate anion and water.

Of course as is well known, iron may exist in the ferrous or ferric state. Either may be utilized to form the cation complexes of the iron methionine complex salts of this invention. If desired, the material utilized as a feed supplement may be a mixture of ferric and ferrous methionine complex salts.

As heretofore previously mentioned, the ferric and ferrous methionine complex salts wherein the cation is a complex of iron and the methionine molecule will provide for better means of iron supplementation and for a better means of methionine supplementation than compounds which are now available. That is, the efficiency of use and body uptake of both the iron and the methionine will be enhanced. The methionine is in the form of a single compound of methionine and is therefore to be distinguished from so-called "proteinates". The term proteinate ordinarily implies that a metal is coordinated with a series of amino acids linked together to provide a protein fraction. Protein molecules for the most part are not absorbed from the intestinal tract. Thus the protein fractions must, before the amino acid can be utilized, be broken down into individual amino acid molecules. With the compounds of the present invention, the methionine is in the form of a single molecule of methionine complexed with the iron ion. Thus the compound, it is believed, need not be further digested prior to absorption but may be absorbed directly through the membranes within the digestive tract.

Importantly, a simple straightforward and economically feasible process of preparing the iron amino acid complex salts of this invention has been developed.

In accord with the process of this invention, iron salts, either in the +3 or the +2 state, are reacted with methionine in the presence of water. pH control has not been found to be particularly important since pH provided by a water solution of these salts is satisfactory for performing the reaction. The quantity of methionine utilized in relation to the molar quantity of the iron cations available will determine whether 1:1 complexes are formed or 1:2 complexes are formed. If 1:1 complexes are desired, 1 mole of iron ion is reacted with 1 mole of methionine. On the other hand, if 1:2 complexes are desired, 1 mole of iron ion is reacted with 2 moles of methionine.

The level of addition of the iron methionine complexes of this invention for use as a feed supplement can vary over a wide range. Preferably the level of addition is such to provide dietary intake of from 50 to 500 parts per million of elemental iron. It should be understood however, that other levels of addition can be utilized and that the precise level of addition is not in fact critical, it being adjusted for the condition of the animals being treated with the nutritional supplement.

The following examples are offered to further illustrate but not limit the preparation of the compounds of this invention.

EXAMPLE 1

(1:1 Ferric Methionine Acid Sulfate)

Ferrous sulfate ($FeSO_4 \cdot 7H_2O$, 27.8 g, 0.1 mole) was mixed with water (5.0 g) and concentrated sulfuric acid (5.1 g). The mixture was thoroughly mixed and treated dropwise with hydrogen peroxide (30% solution, 10.5 g). The addition of hydrogen peroxide resulted in rise in the temperature of the solution and the production of gases. The green color of the ferrous sulfate solution changed to a reddish brown by the addition of $H_2O_2$. The hot solution was treated with dl-methionine (14.9 g) to give a deep reddish clear solution. The solution was concentrated under reduced pressure to 75% its weight and then spread in a thin film on glass plate and heated in an oven at 85° C. for 30 minutes. The dry mass obtained was pulverized to provide a deep red powder of the ferric methionine sulfate.

EXAMPLE 2

(1:1 Ferrous Methionine Acid Sulfate)

Ferrous sulfate ($FeSO_4 \cdot 7H_2O$, 27.8 g, 0.1 mole) was dissolved in water (140 ml) and the solution was heated to 60° C., dl-methionine (14.9 g, 0.1 mole) was added and the mixture was heated at 60° C. until a clear solution was obtained. The solution was evaporated to dryness in vacuo to provide a pale reddish powder which was characterized as ferrous methionine acid sulfate.

EXAMPLE 3

(1:1 Ferric Methionine Chloride)

Ferric chloride ($FeCl_3 \cdot 6H_2O$, 27.0 g, 0.1 mole or $FeCl_3$ anhydrous, 16.2 g, 0.1 mole) was dissolved in water (6.0 g with the hexahydrate and 16.2 g with anhydrous $FeCl_3$). dl-methionine (14.9 g, 0.1 mole) was added to produce a clear deep red solution. Concentration of this solution in vacuo gave a syrup which did not give a crystalline product. The syrup was readily soluble in water. The solution was absorbed on a dry carrier using the following formula.

| | |
|---|---|
| Ferric methionine chloride solution | 1.0 part |
| Bran | 0.5 part |
| Mix thoroughly and evaporated in vacuo to give a dry mix. | |

EXAMPLE 4

(Ferric-Ferrous Methionine Complexes) (10 parts $Fe^{2+}$ and 1 part $Fe^{3+}$)

Ferrous sulfate ($FeSO_4 \cdot 7 H_2$), 27.8 g, 0.1 mole) and ferric chloride ($FeCl_3 \cdot 6H_2O$, 2.8 g, 0.01 mole) were added to water (30 ml). The mixture was heated at 60° C. until complete solution was obtained. dl-methionine was added (16.4 g, 0.11 mole) and it was heated at 60° C. until a solution was obtained. The red solution was concentrated under reduced pressure to provide a free-flowing powder of the ferrous-ferric methionine sulfate.

EXAMPLE 5

(Ferrous-Ferric Methionine Sulfate Complex)

Ferric sulfate (20.1 g, 0.1 mole) and ferrous sulfate ($FeSO_4 \cdot H_2O$, 19 g., 0.1 mole) were dissolved in 60 ml of water. dl-methionine (30 g, 0.2 mole) was added to the solution and the mixture heated at 60° C. until complete dissolution of dl-methionine occurred. The red solution was concentrated under reduced pressure to provide a free-flowing powder of the ferrous-ferric methionine sulfate.

These compounds may be used per se as feed supplements or they may be mixed with suitable carriers. The carrier should be inert to the active compound, biodegradable and digestible and is preferably water soluble.

What is claimed is:

1. A feed supplement having the capability of enhancing the nutrition and health of animals by effectively increasing the absorption, distribution and utilization of iron and methionine within the body system of said animals, comprising in solid form a water soluble iron methionine complex salt having an anion selected from the group consisting of halide, phosphate and sulfate, the amount of said salt being sufficient to provide a dietary intake of iron of at least from about 50 parts per million to about 500 parts per million.

2. The feed supplement of claim 1 wherein said iron methionine complex salt is a mixture of 1:1 ferric methionine chloride, 1:1 ferric methionine acid sulfate and 1:1 ferrous methionine acid sulfate.

3. A water soluble methionine ferric ion complex salt in solid form, of the formula

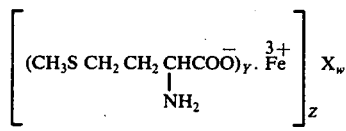

wherein Y is a whole integer and is 1 or 2, X is an inorganic anion selected from the group consisting of halide, sulfate and phosphate, and Z and W are whole integers selected to electrostatically balance the cationic and anionic charges of the complex salt.

4. The complex salts of claim 3 wherein Y is 1, said salt therefore being a 1:1 ratio complex salt of methionine and the ferric ion.

5. The complex salts of claim 3 wherein Y is 2, said salts therefore being 1:2 ratio complex salt of the ferrous ion and methionine.

6. A water soluble methionine ferrous ion complex salt, in solid form, of the formula

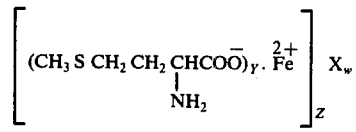

wherein Y is a whole integer and is 1 or 2, X is an inorganic anion selected from the group consisting of halide, sulfate, and phosphate, and Z and W are whole integers selected to electrostatically balance the cationic and anionic charges of the complex salt.

7. The complex salts of claim 6 wherein Y is 1, said salt therefore being a 1:1 ratio complex salt of methionine and the ferrous ion.

8. The complex salts of claim 6 wherein Y is 2, said salt therefore being 1:2 ratio complex salt of methionine and the ferrous ion.

9. 1:1 ferric methionine chloride in solid form.

10. 1:1 ferric methionine acid sulfate in solid form.

11. 1:1 ferrous methionine acid sulfate in solid form.